US00PP12194P2

(12) United States Plant Patent
Hanes

(10) Patent No.: US PP12,194 P2
(45) Date of Patent: Nov. 6, 2001

(54) VERBENA PLANT NAMED 'TORT PEACHY'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/378,573

(22) Filed: Aug. 20, 1999

(51) Int. Cl.[7] ..... A01H 5/00
(52) U.S. Cl. ..... Plt./308
(58) Field of Search ..... Plt./308

(56) References Cited

PUBLICATIONS

GTITM UPOVROM citation for 'Tort Peachy' as per QZ PBR 980460; Mar. 31, 1998.*

* cited by examiner

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new and distinct cultivar of verbena plant as herein shown and described, named 'Tort Peachy', that is characterized by its green foliage with peach flowers on a prostrate branching plant; its fast rooting and vigorous growth.

2 Drawing Sheets

BACKGROUND OF THE NEW PLANT

The present invention comprises a new and distinct cultivar of verbena, botanically known as *Verbena hybrida*, and hereinafter referred to by the cultivar name 'Tort Peachy'.

The new cultivar is propagated asexually from vegetative cuttings in Gilroy, Calif. The new cultivar is propagated from a seedling selected from a population grown from a self-pollinated plant with the pedigree of: an unnamed plant (unpatented).

The new cultivar was created in Gilroy, Calif., and has been repeatedly asexually reproduced by cuttings over a two-year period. The new cultivar has also been trialed at many locations in the United States and in Europe. The new cultivar has been found to retain its distinctive characteristics and reproduces true to type through successive propagations, and this novelty is firmly fixed.

DESCRIPTION OF THE DRAWING

The new verbena plant is illustrated by the accompanying photograph, the colors shown being as true as can be reasonably obtained by conventional photographic procedures.

DESCRIPTION OF THE NEW CULTIVAR

Figure 1:
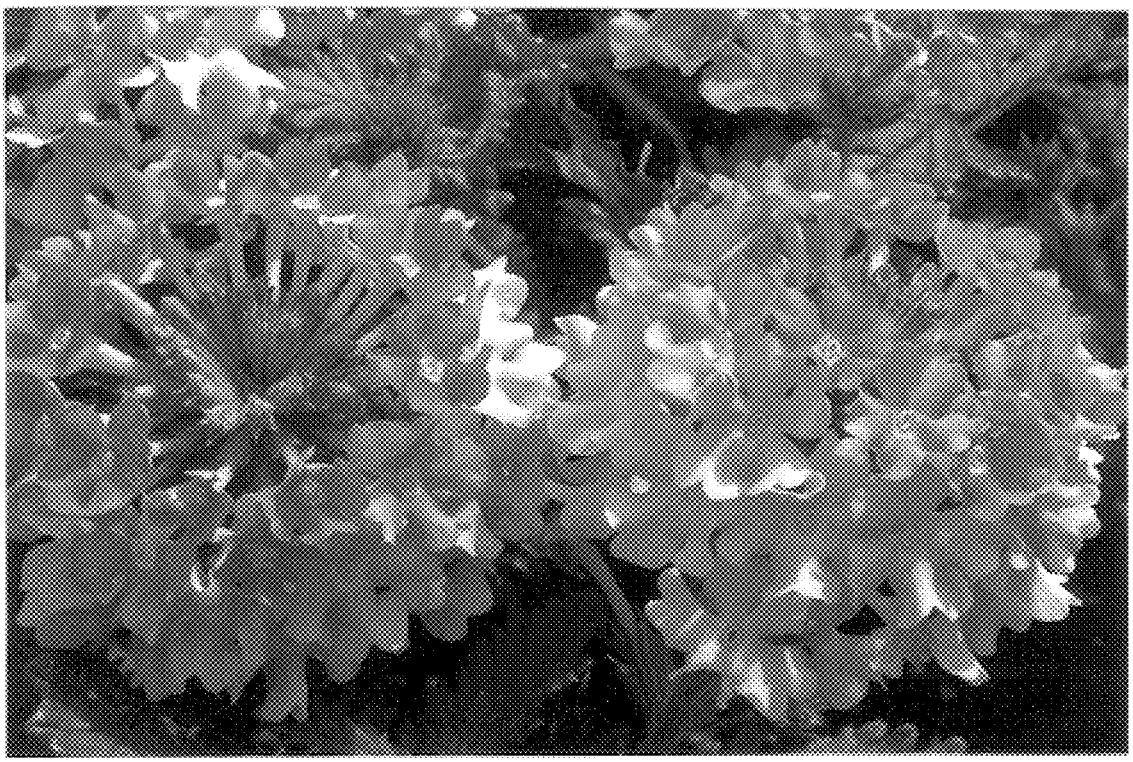
FIG. 1 depicts inflorescences, buds and foliage.
Figure 2:
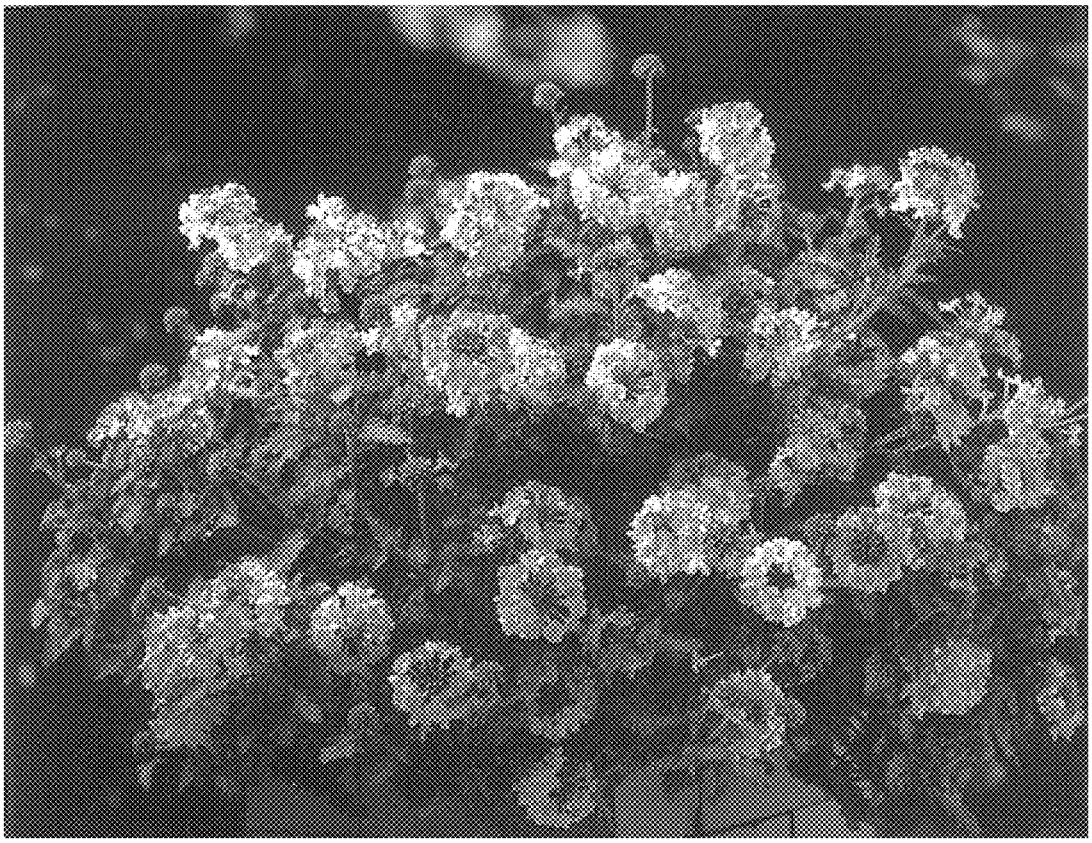
FIG. 2 shows the overall mature plant.

The following detailed descriptions set forth the distinctive characteristics of 'Tort Peachy'. The data, which defines these characteristics, was collected from asexual reproductions carried out in Gilroy, Calif. The plant history was taken on 20-week-old plants, blossomed under natural light in a greenhouse and color readings were taken under ambient light. Color references are primarily to The R.H.S. Colour Chart of The Royal Horticultural Society of London (R.H.S.).

The Plant

Classification:
- *Botanical.*—*Verbena hybrida.*
- *Commercial.*—Verbena.

Parentage: Unnamed plant (unpatented).

Form: Moderately upright with prominent lateral expansion.

Height: 14–18 cm from soil level to top of blooms, 95 cm. wide.

Winter hardiness: Withstands temperatures to 32–34 degrees F.

Leaves:
- *Length.*—3.9 cm.
- *Width.*—1.7 cm.
- *Texture.*—Upper surface moderately hairy; under surface slightly hairy.
- *Color.*—Upper side: Green 137A. Under side: Green 137C.

Foliage:
- *Shape.*—Ovate-lanceolate.
- *Apex.*—Obtuse.
- *Base.*—Truncate.
- *Venation.*—Pinnatifid, coloration of upper veins and ribs are green RHS 137A, coloration of lower ribs is yellow-green RHS 147C with RHS 137C veins; Margin is irregularly crenately incised.

Petioles:
- *Length.*—4–6 mm.
- *Diameter.*—2 mm.
- *Color.*—Yellow-green RHS 147C.

Stems:
- *Length.*—9–28 cm.
- *Diameter.*—1–2 mm.
- *Texture.*—Pubescent.
- *Internode length.*—1.5–2.0 cm.
- *Color.*—Upper: Yellow-green RHS 144A; Lower: Yellow-green RHS 144B.

Roots: Initiates roots in 5 days under greenhouse conditions.

The Flower

Blooming habit: Flowers continuously throughout the year.

Period of time to produce a flowering plant: In a greenhouse, 6–8 weeks in a 4 inch pot or 8–12 weeks in a 10 inch hanging basket.

Color: The color of the flower fades over time and in response to the amount and quality of light. Typical flower color when the flower first opens is 42A upper and 32B lower then fades to 32A upper and 32C lower then fades to 29B upper and 29C lower then fades to 29C upper and 29D lower. A small "eye" at the base of the petals has a color of 145C.

Spike: Approximately 5.3 cm. diameter; depth approximately 3–3.5 cm.

Floret: Approximately 1.5 cm diameter.

Petals: The corolla has a limb of five petals (lobes) fused at the base.

*Diameter of the limb.*—1.5 cm.
*Length of one lobe.*—6–7 mm.
*Width of one lobe.*—8 mm.
*Shape.*—Broad, obovate.
*Apex.*—Obtuse, deeply notched, base is fused to the corolla tube.
*Margin.*—Entire.
*Texture.*—Soft and satiny.

Sepals: Five fused sepals that form a calyx which sheathes the corolla tube and one smaller sepal (5 mm in length; 2–3 mm width; apex is aristate/cuspidate and base is truncate) attached to the base of the calyx;

*Length.*—1 cm.
*Width.*—3 mm.
*Shape of calyx and sepals.*—Linear.
*Apex.*—Acute.
*Color.*—Yellow-green RHS 144A for both surfaces.

Peduncles:

*Length.*—5–8 cm.
*Diameter.*—3 mm.
*Texture.*—Pubescent.
*Color.*—Yellow-green RHS 146B.

Buds:

*Length.*—5–8 mm.
*Diameter.*—1–2 mm.
*Shape.*—Linear.
*Color.*—Red group RHS 43C immediately before opening.

Lastingness of the individual blooms: 7–19 days depending on environmental conditions.

Fragrance: None.

Type: A spike composed of approximately 25 flowers.

Reproductive Organs

Filaments are fused with the corolla; four anthers with two pollen sacs per anther; produces a moderate amount of pollen which is light yellow RHS 11B; one stigma yellow-green RHS 144A; one style approximately 1 cm in length, slightly curved at the tip with a yellow-green color RHS 145A; one pistil; one ovary which is not deeply lobed.

Fruit: Does not freely set seed but occasionally produces four narrow nutlets approximately 4 mm long; colored grey-brown RHS 199D and enclosed in the dried calyx.

Disease and Insect Resistance

No susceptibility to diseases or insects noted to date.

Comparison with Parental Cultivar

The parental cultivar was a scarlet-flowered verbens, however there were numerous differences. 'Tort Peachy' has a more branched, upright spreading plant habit than the parental cultivar. 'Tort Peachy' also is more free flowering and flowers earlier than the parental cultivar.

I claim:

1. A new and distinct Verbena plant, as illustrated and described.

* * * * *